US012138025B2

(12) United States Patent
Kobayashi et al.

(10) Patent No.: US 12,138,025 B2
(45) Date of Patent: Nov. 12, 2024

(54) BLOOD PRESSURE MEASUREMENT DEVICE AND CUFF UNIT

(71) Applicant: OMRON HEALTHCARE Co., Ltd., Kyoto (JP)

(72) Inventors: Tatsuya Kobayashi, Kyoto (JP); Yohei Asano, Kyoto (JP); Yasuhiro Kawabata, Kyoto (JP); Hideyuki Yamashita, Kyoto (JP); Akito Ito, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 975 days.

(21) Appl. No.: 17/148,921

(22) Filed: Jan. 14, 2021

(65) Prior Publication Data

US 2021/0127996 A1     May 6, 2021

Related U.S. Application Data

(63) Continuation of application No. PCT/JP2019/026088, filed on Jul. 1, 2019.

(30) Foreign Application Priority Data

Jul. 20, 2018     (JP) .................................. 2018-136925

(51) Int. Cl.
  *A61B 5/22* (2006.01)
  *A61B 5/021* (2006.01)
  *A61B 5/022* (2006.01)
  *A61B 5/0235* (2006.01)

(52) U.S. Cl.
  CPC ........ *A61B 5/02233* (2013.01); *A61B 5/0235* (2013.01)

(58) Field of Classification Search
  CPC .............. A61B 5/02233; A61B 5/0235; A61B 5/02141; A61B 5/00; A61B 5/02; A61B 5/022; A61B 5/021–022; A61B 2562/0247; A61B 5/6823
  See application file for complete search history.

(56) References Cited

U.S. PATENT DOCUMENTS

| 4,779,626 | A | 10/1988 | Peel et al. | |
|---|---|---|---|---|
| 2012/0253210 | A1* | 10/2012 | Uesaka | A61B 5/022 600/499 |
| 2015/0201851 | A1 | 7/2015 | Kubo | |

FOREIGN PATENT DOCUMENTS

| CN | 115243607 A | * | 10/2022 | ......... A61B 5/02233 |
|---|---|---|---|---|
| EP | 465345 A1 | | 1/1992 | |
| EP | 2898824 A1 | | 7/2015 | |
| JP | 62-133933 A | | 6/1987 | |
| JP | 63-68133 A | | 3/1988 | |
| JP | 4-64334 A | | 2/1992 | |
| JP | 2006346451 A | * | 12/2006 | ............ A61M 39/08 |

(Continued)

OTHER PUBLICATIONS

English Translation CN 115243607 A, Omron Healthcare Co Ltd, 30 pages, printed on Feb. 21, 2024, (Year: 2022).*

(Continued)

*Primary Examiner* — Matthew Kremer
*Assistant Examiner* — Jennifer Grace Baires-Tweed
(74) *Attorney, Agent, or Firm* — Wenderoth, Lind & Ponack, L.L.P.

(57) ABSTRACT

A blood pressure measurement device that measures blood pressure, and relates to a cuff unit.

20 Claims, 11 Drawing Sheets

(56) References Cited

FOREIGN PATENT DOCUMENTS

| | | | | |
|---|---|---|---|---|
| JP | 2009-217703 | A | | 9/2009 |
| JP | 2014-68825 | A | | 4/2014 |
| JP | 2014068825 | A | * | 4/2014 |
| JP | 2015-136484 | A | | 7/2015 |
| WO | WO-2009130635 | A1 | * | 10/2009 ......... A61B 5/02141 |

OTHER PUBLICATIONS

English Translation JP 2014068825 A, Omron Healthcare Co Ltd, 16 pages, printed on Feb. 21, 2024, (Year: 2014).*
English Translation JP 2006346451 A, Smiths Medical Deutschland GmbH, pages, printed on Feb. 21, 2024, (Year: 2006).*
International Preliminary Report on Patentability and Written Opinion of the International Searching Authority issued Feb. 4, 2021 in International (PCT) Patent Application No. PCT/JP2019/026088.

* cited by examiner

[FIG. 1]
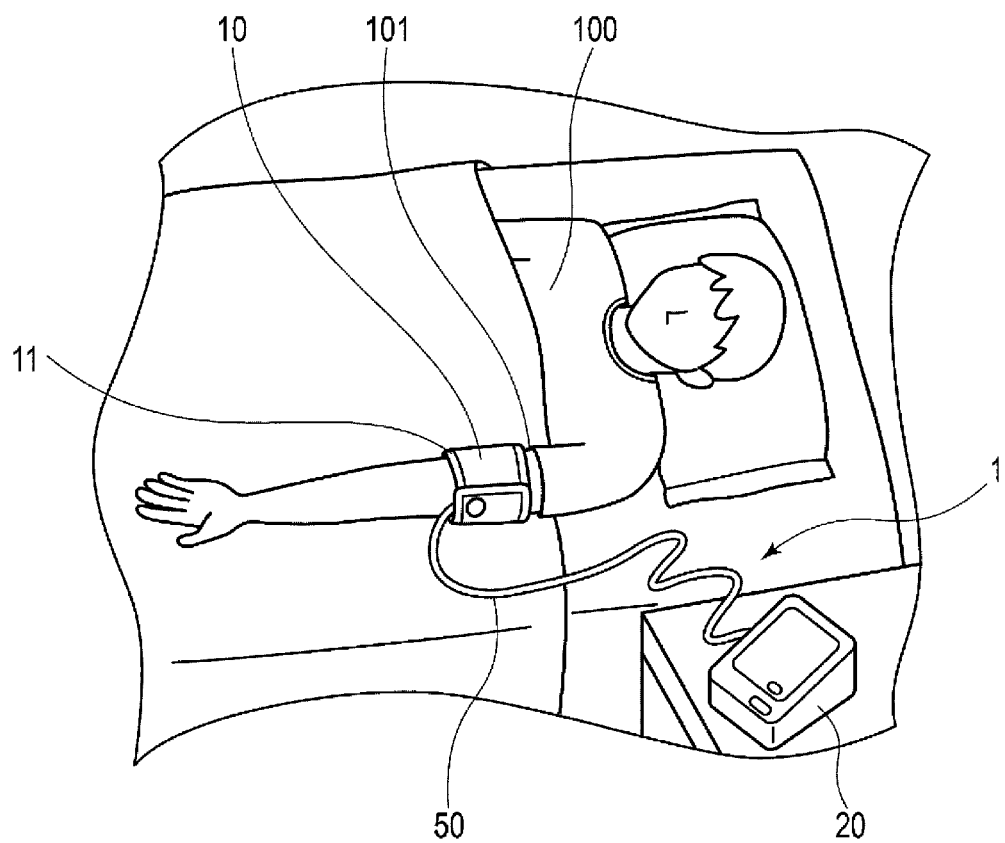

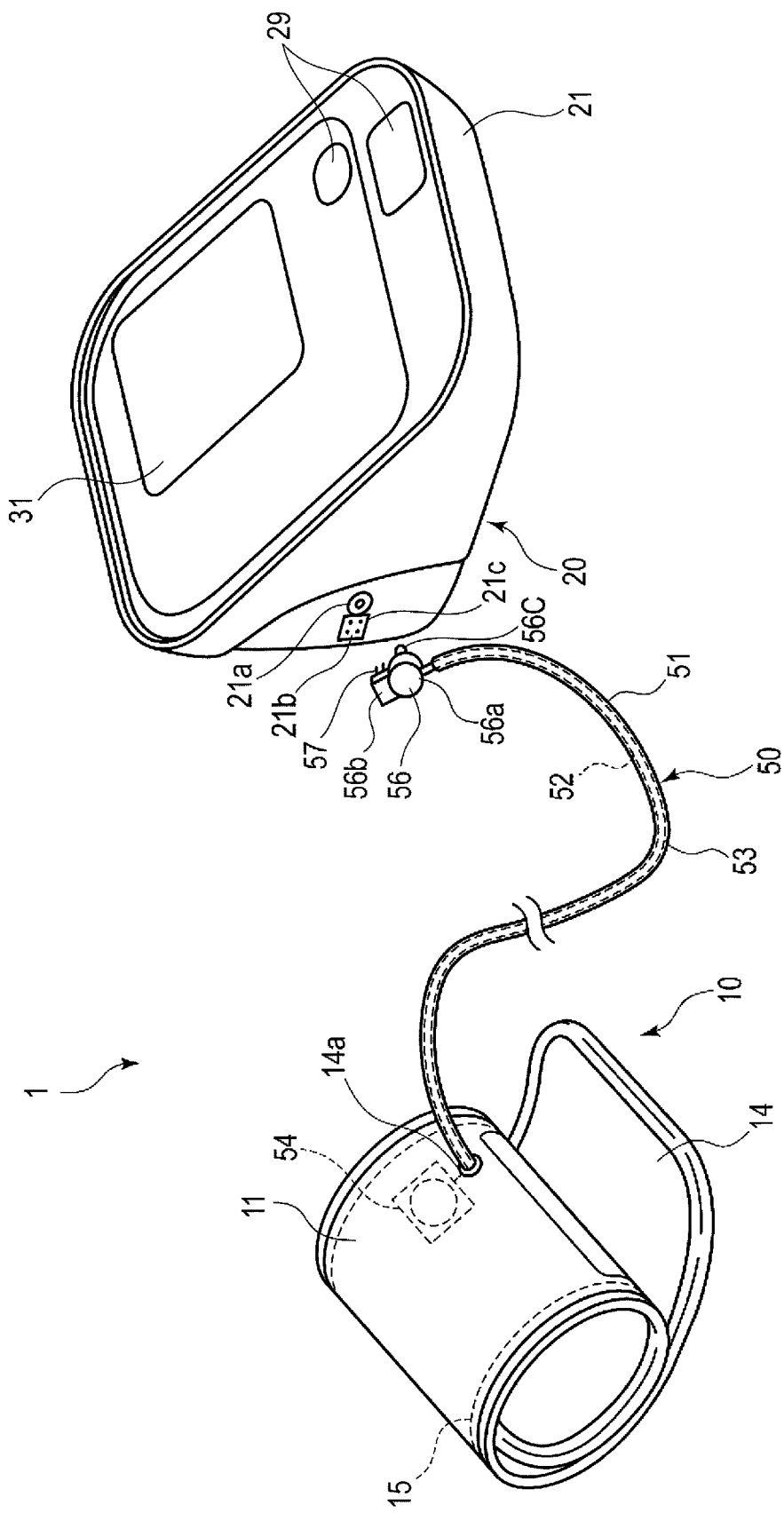
[FIG. 2]

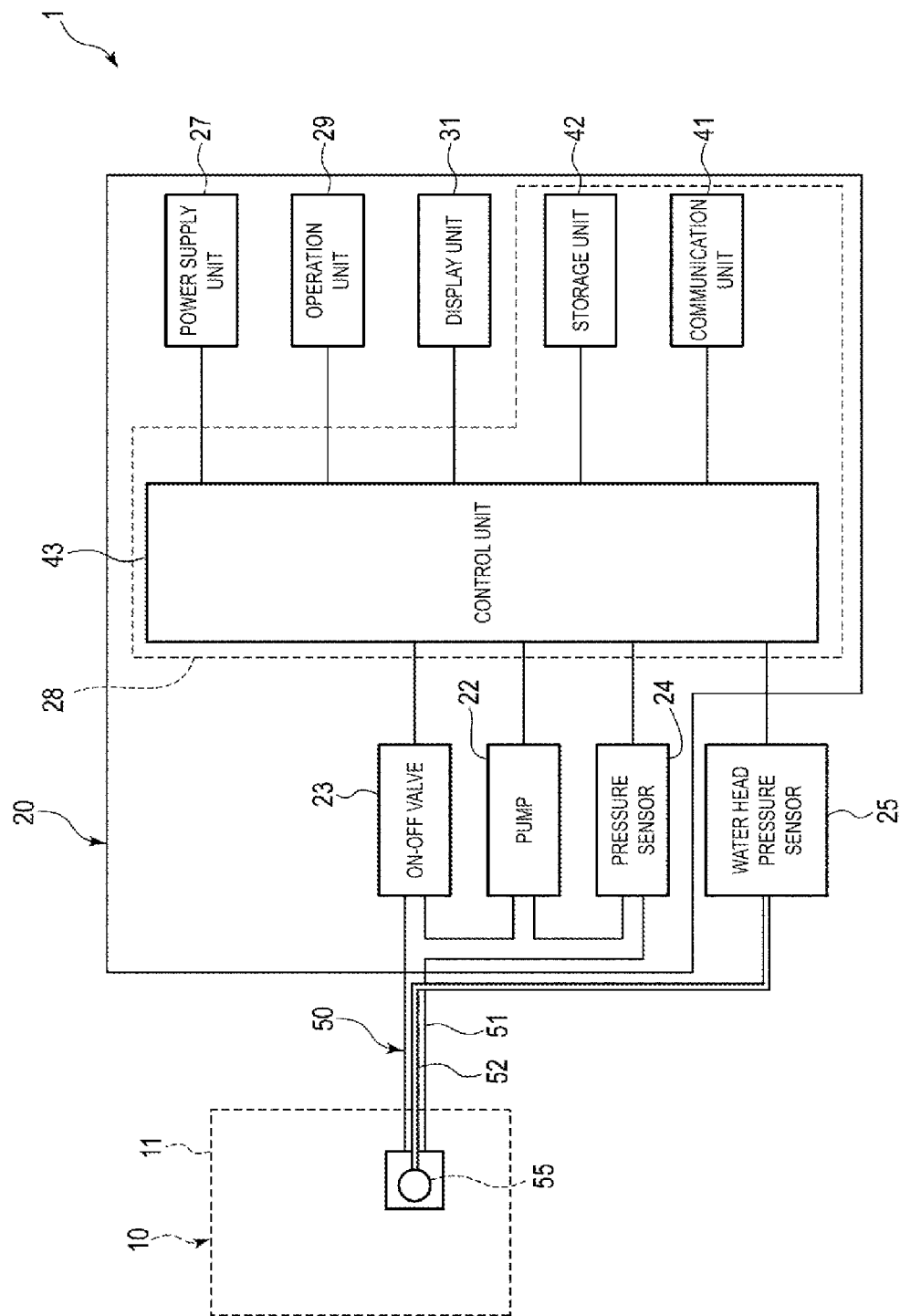
[FIG. 3]

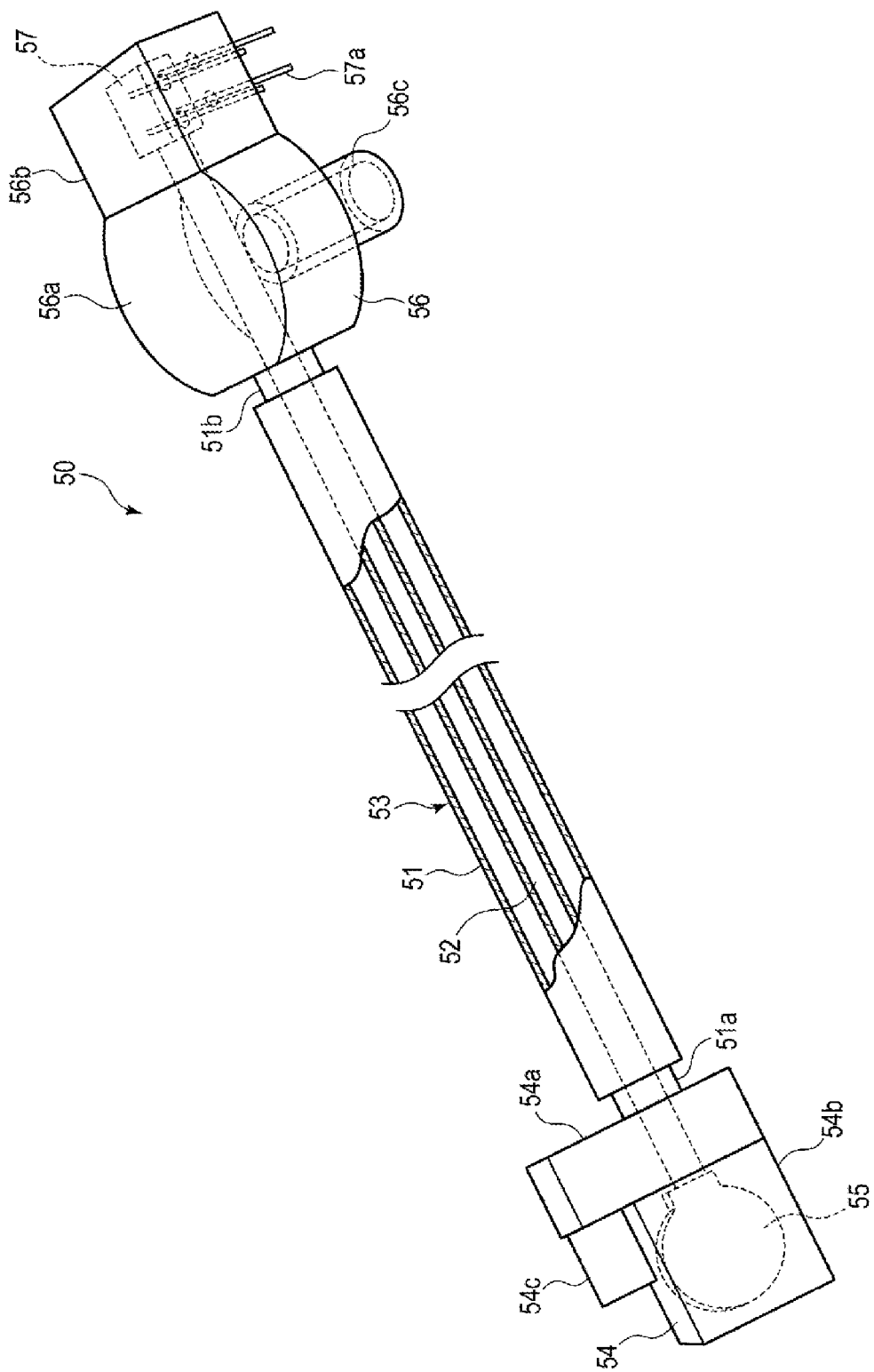
[FIG. 4]

[FIG. 5]
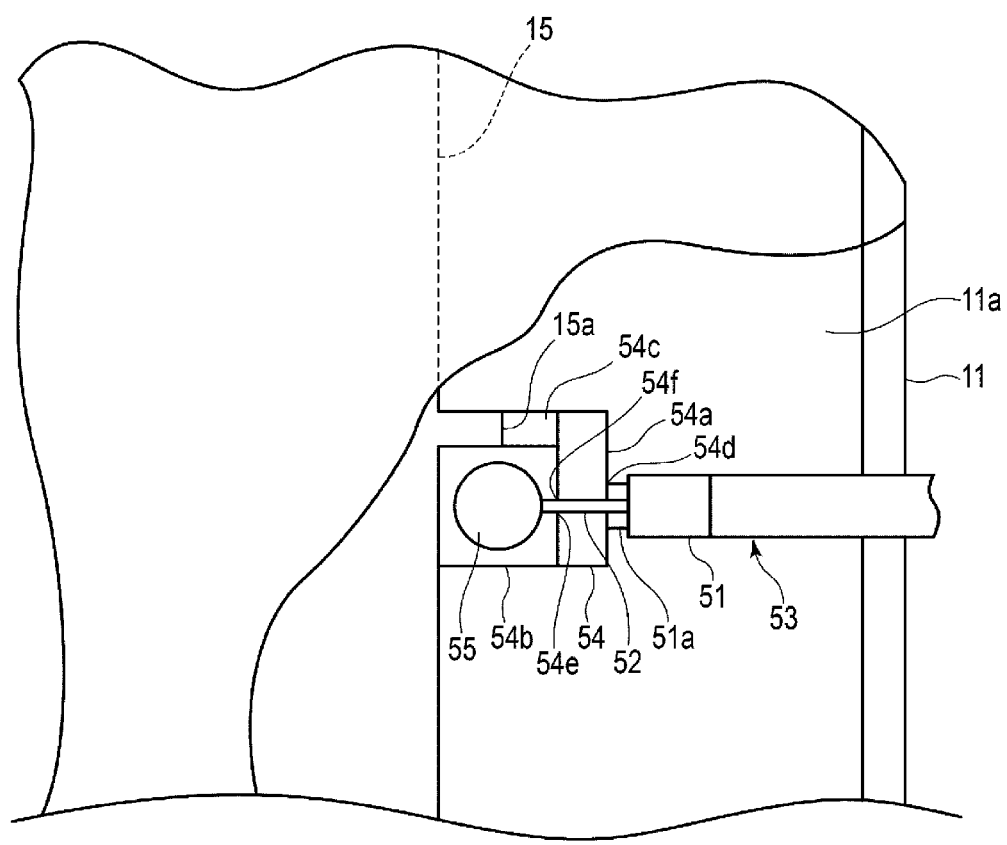

[FIG. 6]
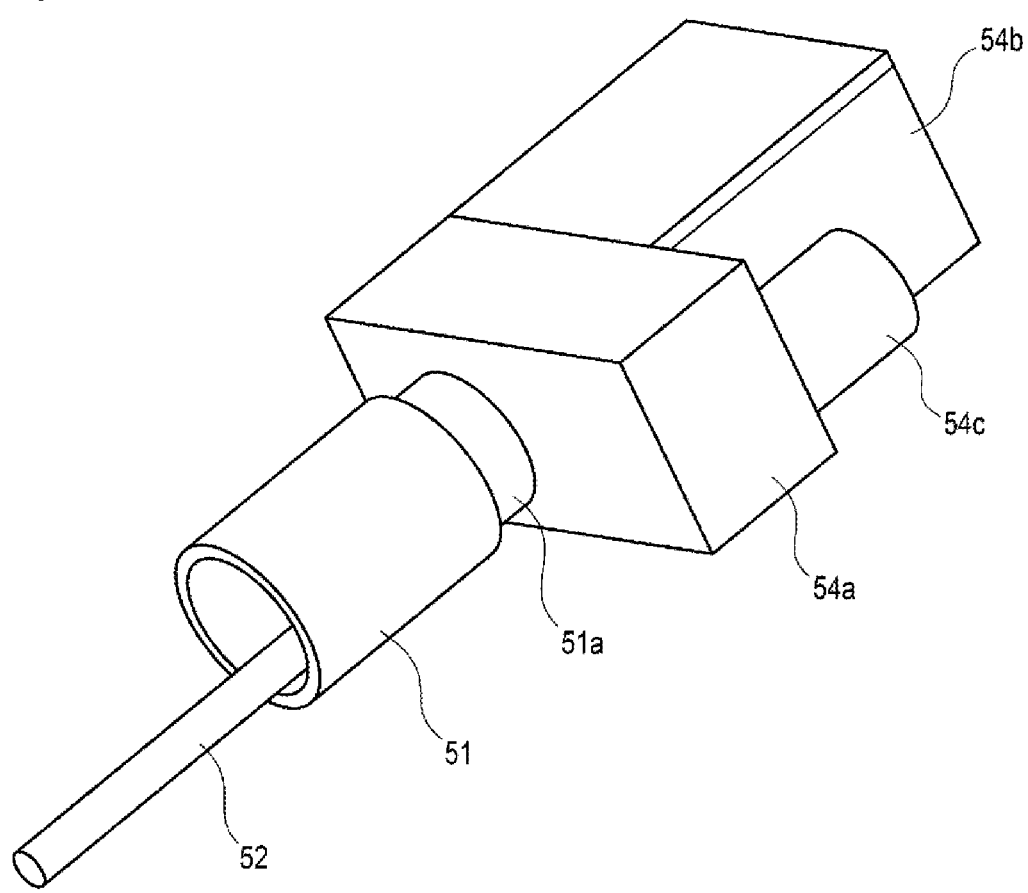

[FIG. 7]
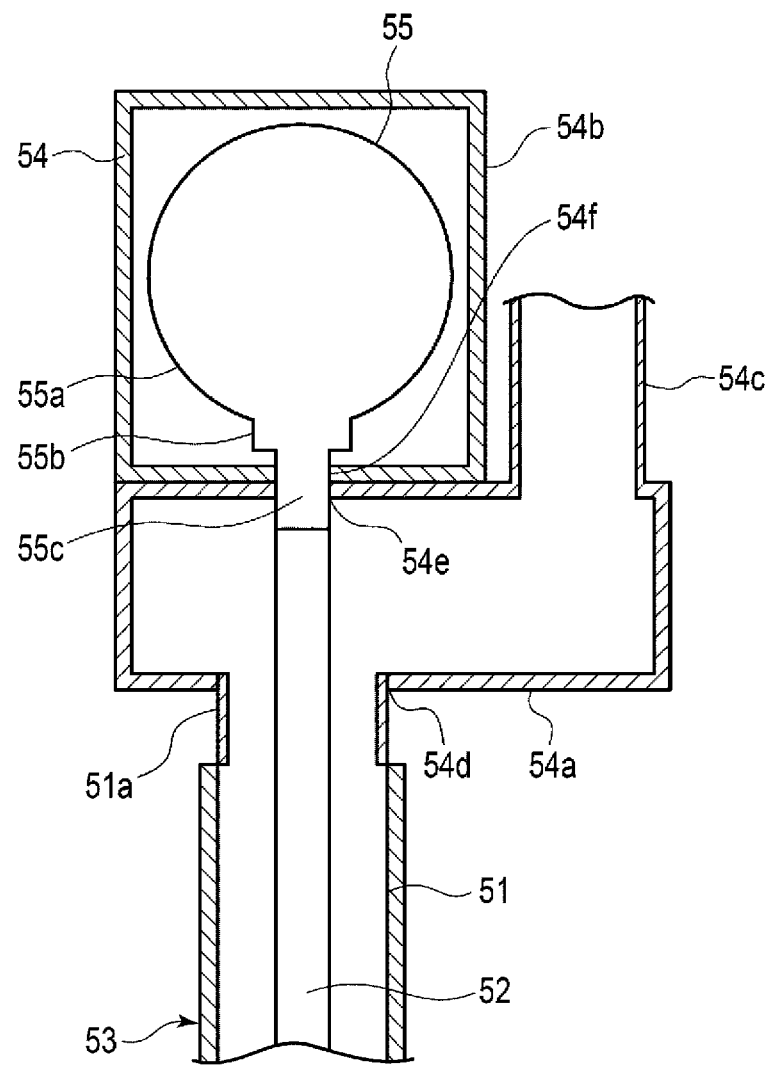

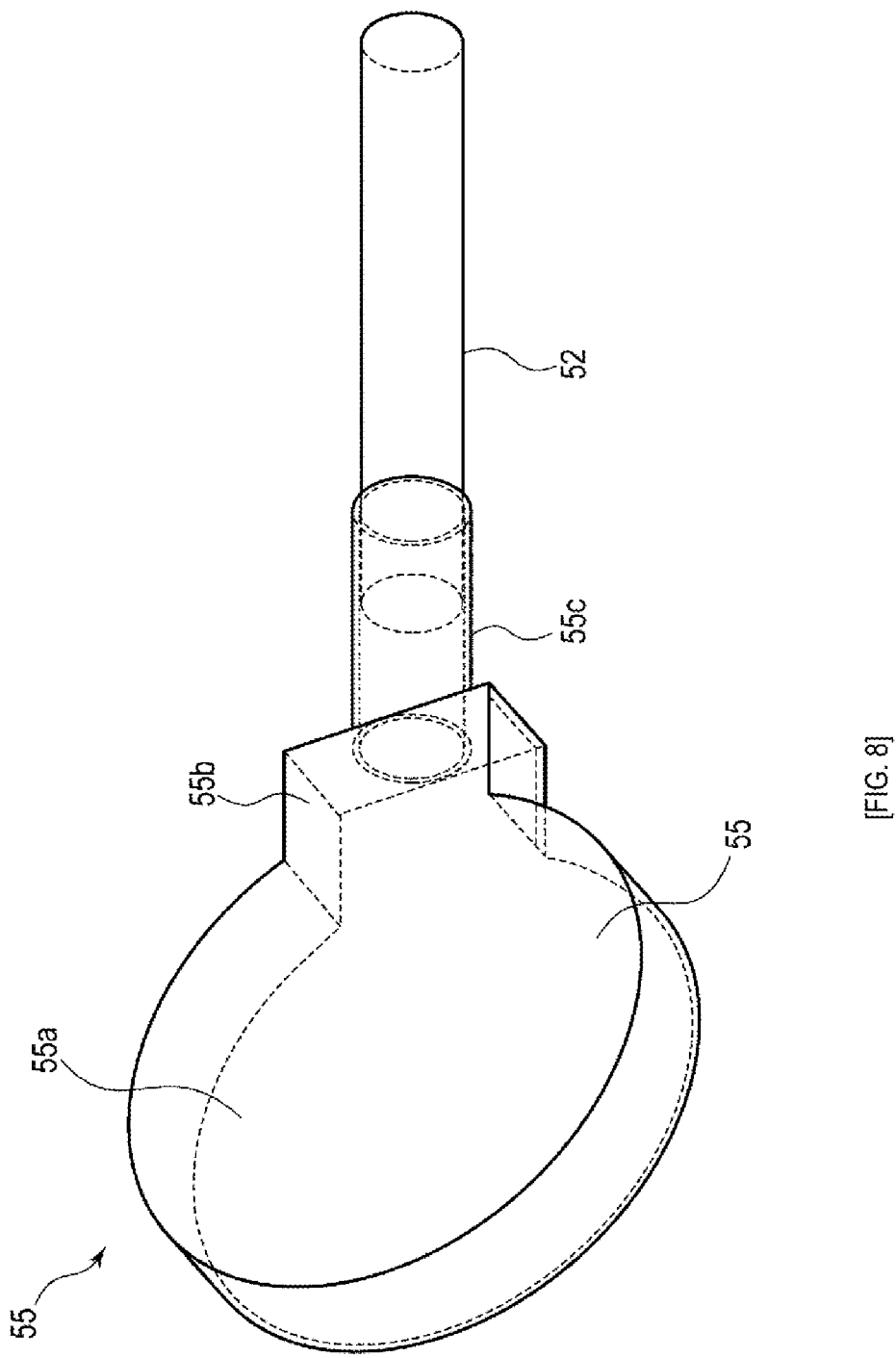
[FIG. 8]

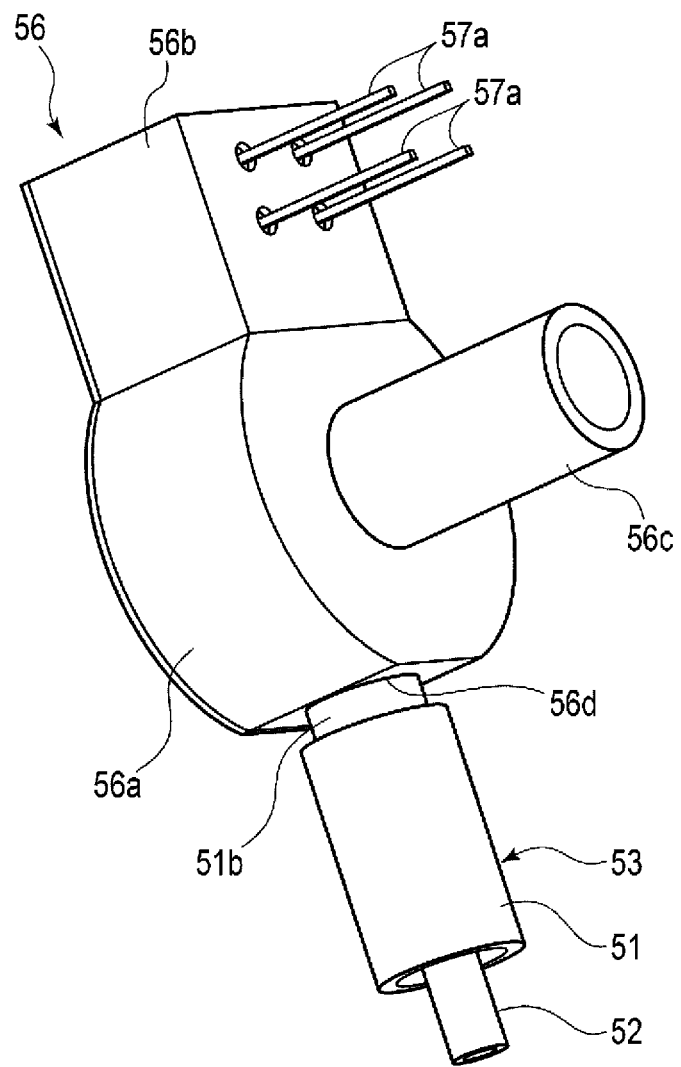
[FIG. 9]

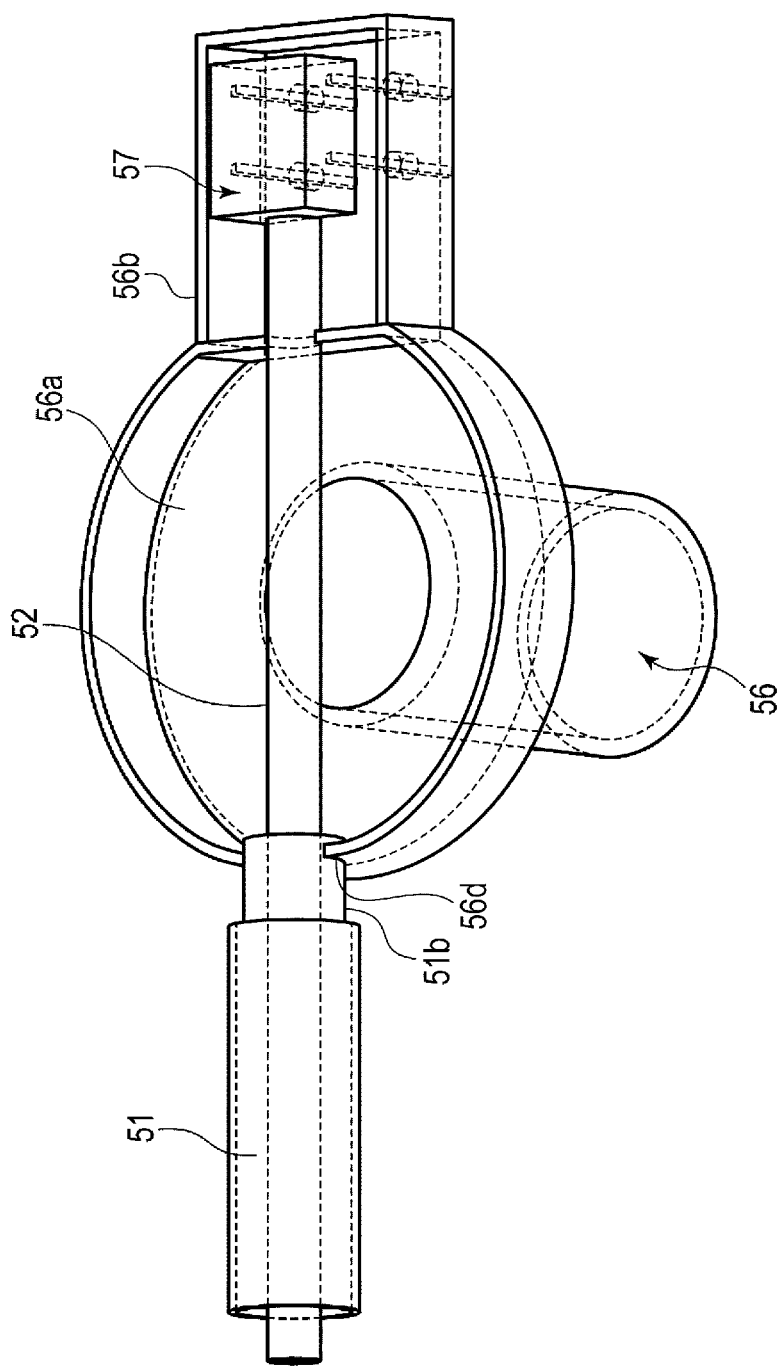

[FIG. 11]
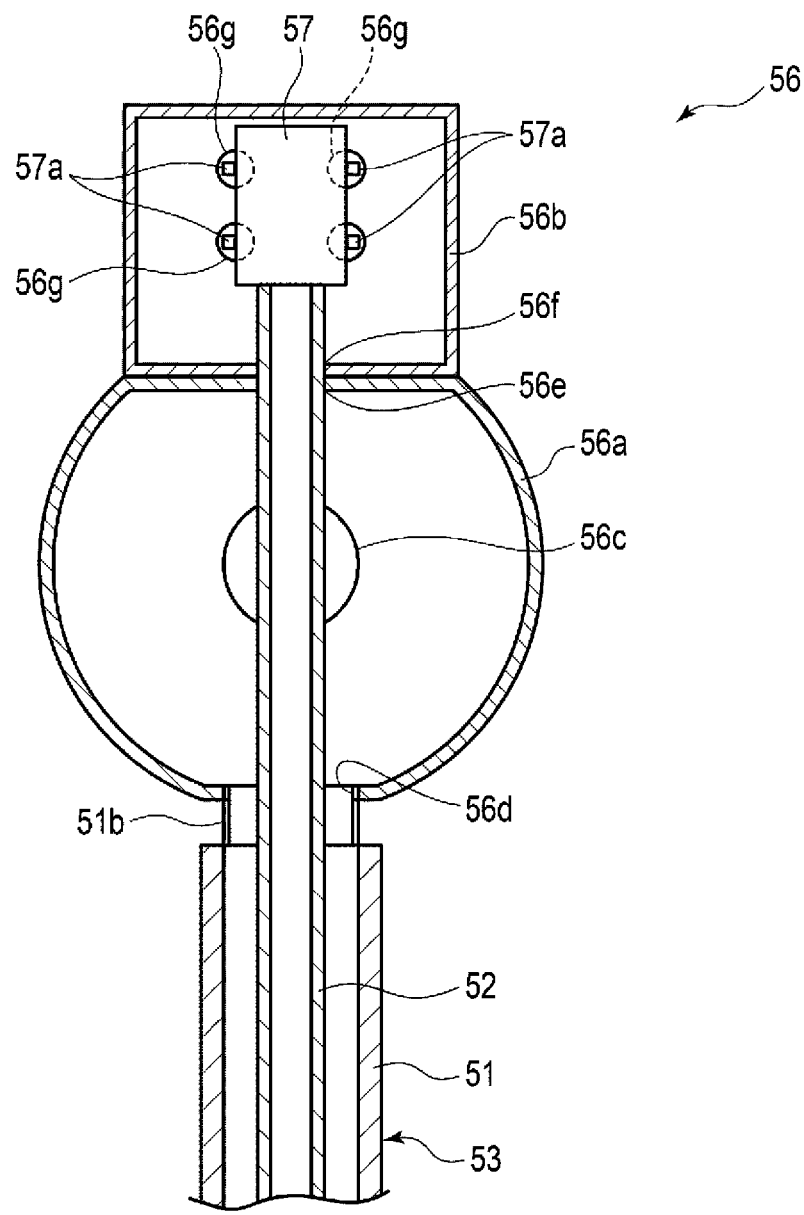

BLOOD PRESSURE MEASUREMENT DEVICE AND CUFF UNIT

CROSS-REFERENCE TO RELATED APPLICATIONS

This application is the U.S. national stage application filed pursuant to 35 U.S.C. 365(c) and 120 as a continuation of International Patent Application No. PCT/JP2019/026088, filed Jul. 1, 2019, which application claims priority from Japanese Patent Application No. 2018-136925, filed Jul. 20, 2018, which applications are incorporated herein by reference in their entireties.

TECHNICAL FIELD

The present invention relates to a blood pressure measurement device that measures blood pressure, and relates to a cuff unit.

BACKGROUND ART

In recent years, a blood pressure measurement device used for measuring blood pressure has been utilized to confirm a health state not only in a medical institution but also at home. The blood pressure measurement device includes, for example, a cuff including an internal space that is wrapped around an upper arm or a wrist of a living body, and a device body including a pump that feeds fluid to the internal space of the cuff, and a pressure sensor. For example, measurement of blood pressure by the blood pressure measurement device is performed by wrapping the cuff around an upper arm or a wrist of a living body, inflating and deflating the cuff, and detecting pressure of the cuff by the pressure sensor (see, for example, Patent Document 1).

Generally, in the blood pressure measurement device, it is said that a blood pressure value measured at the same height as the height of a position of a heart of a subject approximates to a blood pressure value in the heart. Thus, in an upper-arm blood pressure measurement device including a cuff to be wrapped around an upper arm, measurement is generally performed in a posture in which an arm is placed on a desk with an elbow in a bent position.

Additionally, in regard to timing for blood pressure measurement, the blood pressure measurement is performed not only in the morning and the evening but also during sleep.

CITATION LIST

Patent Literature

Patent Document 1: JP 2009-217703 A

SUMMARY OF INVENTION

Technical Problem

In such blood pressure measurement, when a posture of a subject changes, the relationship between a position of the blood pressure measurement and a position of the sensor changes. For example, during sleep, a posture of a subject tends to change and positional relationship between the cuff and the sensor tends to vary. Due to such circumstances, it is conceivable to detect the positional relationship between the cuff and the sensor, and correct a blood pressure measurement result according to the positional relationship between the cuff and the sensor. However, in a case where tubing for height detection is provided in addition to tubing for cuff connection that connects the cuff and the device body, the number of lines of tubing increases and thus a tubing structure and connection work become complicated, and handling becomes difficult.

Then, an object of the present invention is to provide a blood pressure measurement device that can simplify a tubing structure and that provides high usability.

Solution to Problem

According to an aspect, provided is a blood pressure measurement device including a cuff including a bag body including an internal space in which first fluid is disposed, the cuff being wrapped around a living body, a device body including a pressure sensor configured to detect pressure of the first fluid in a flow path communicating with the internal space of the bag body, a first tube constituting a first flow path through which the first fluid passes, the first tube including a first end side connected to the bag body and a second end side connected to the device body, a second tube disposed in the first flow path in the first tube and constituting a second flow path through which second fluid passes, a water head pressure bag provided in a first end side of the second tube and accommodating the second fluid, the water head pressure bag being attached to the cuff, and a water head pressure sensor provided in a second end side of the second tube and configured to detect pressure of the second fluid.

Here, the cuff refers to a cuff wrapped around an upper arm or the like of a living body when blood pressure is measured, and is inflated by feeding of fluid. The cuff is provided, for example, in a blood pressure measurement device that measures blood pressure at an upper arm. Additionally, here the cuff may refer to a bag-like structure such as an air bag, or may be a structure in which a bag-like structure such as an air bag is accommodated in a bag-like cover. Additionally, here, the device body refers to a processing device of a blood pressure measurement device including a pump and a flow path.

According to this aspect, the second tube through which the second fluid for water head pressure detection passes is disposed in the first flow path of the first tube through which the first fluid passes, and a tube for blood pressure measurement and a tube for water head pressure measurement are combined into a dual tube structure. Thus, the number of lines of tubing can be reduced, and usability improves.

In the blood pressure measurement device of an aspect described above, the water head pressure sensor is attached to the device body, the second fluid has a smaller compression rate than a compression rate of the first fluid, and the second tube has a smaller flow path diameter and higher bending rigidity than a flow path diameter and bending rigidity of the first tube.

According to this aspect, the second tube in which the second fluid having a small compression rate is disposed is disposed through an inside of the first tube through which the first fluid having a large compression rate passes, and thus deformation of the second tube can be prevented and water head pressure detection accuracy can be maintained. Moreover, the first tube can be bent, and thus handleability can be ensured. Additionally, an outer periphery of the second tube is protected by a layer of the first fluid, and thus damage can be prevented.

In the blood pressure measurement device according to an aspect described above, the device body includes a flow path portion connected to the internal space of the bag body via the first tube, a pump configured to feed the first fluid to the bag body via the flow path portion, an on-off valve configured to open and close the flow path portion, a control unit configured to control operations of the pump and the on-off valve, and a housing including an outer surface provided with a connecting portion to which a tube unit including the first tube and the second tube is connected.

According to this aspect, the outer surface of the housing of the device body is provided with the connecting portion to which the tube unit is connected, and thus connection work of tubing becomes easy.

The blood pressure measurement device according to an aspect described above integrally includes a first case body and a second case body, the first case body is connected to the first end side of the first tube and includes a space in which the first tube communicates with the internal space of the bag body, the second case body accommodates the water head pressure bag connected to the first end side of the second tube, and the blood pressure measurement device includes a first connector attached to the cuff.

According to this aspect, the first connector including the first case body and the second case body is provided, and thus connection work of the first tube and the second tube becomes easy.

The blood pressure measurement device of an aspect described above integrally includes a third case body and a fourth case body, the third case body is connected to the first tube and forms a flow path in which the flow path portion in the device body communicates with the first tube, the fourth case body accommodates the water head pressure sensor connected to the second tube, and the blood pressure measurement device includes a second connector connected to the device body.

According to this aspect, the second connector includes the third case body and the fourth case body, and thus connection work of the first tube and the second tube becomes easy.

In the blood pressure measurement device of an aspect described above, the third case body includes a plug having a tubular shape and protruding outward, and the water head pressure sensor includes a terminal protruding from the fourth case body in a protruding direction of the plug.

According to this aspect, in the second connector, the plug and the terminal protrude in the same direction, and thus electric connection and connection of the flow path of the first fluid can be performed by a single connection operation, and workability and handleability improve.

In the blood pressure measurement device of an aspect described above, the first fluid is air, and the second fluid is glycerin.

According to this aspect, glycerin having low volatility is used, and thus incorporation of air is prevented, and high detection accuracy can be maintained.

According to an aspect, provided is a cuff unit including a cuff connected to a device body and including a bag body including an internal space in which first fluid is disposed, the cuff being wrapped around a living body, a first tube constituting a first flow path through which the first fluid passes, the first tube including a first end side connected to the bag body and a second end side connected to the device body, a second tube disposed in the first flow path in the first tube and constituting a second flow path through which second fluid passes, a water head pressure bag provided in a first end side of the second tube and accommodating the second fluid, the water head pressure bag being attached to the cuff, and a water head pressure sensor provided in a second end side of the second tube and configured to detect pressure of the second fluid.

According to this aspect, the second tube through which the second fluid for water head pressure detection passes is disposed in the first flow path of the first tube through which the first fluid passes, and a tube for blood pressure measurement and a tube for water head pressure measurement are combined into a dual tube structure. Thus, the number of lines of tubing can be reduced, and usability improves.

Advantageous Effects of Invention

The present invention can provide a blood pressure measurement device and a cuff unit that can simplify a tubing structure and that provide high useability.

BRIEF DESCRIPTION OF DRAWINGS

FIG. 1 is an explanatory view illustrating a configuration of a blood pressure measurement device according to a first embodiment of the present invention.

FIG. 2 is a perspective view illustrating the configuration of the blood pressure measurement device.

FIG. 3 is a block diagram illustrating the configuration of the blood pressure measurement device.

FIG. 4 is a partial cross-sectional perspective view illustrating a configuration of a height detection unit of the blood pressure measurement device.

FIG. 5 is a plan view illustrating a configuration of a first connector of the blood pressure measurement device.

FIG. 6 is a perspective view illustrating a configuration of the first connector.

FIG. 7 is a cross-sectional view illustrating the configuration of the first connector.

FIG. 8 is a perspective view illustrating a configuration of a water head pressure bag of the blood pressure measurement device.

FIG. 9 is a perspective view illustrating a configuration of a second connector of the blood pressure measurement device.

FIG. 10 is an explanatory view illustrating an internal configuration of the second connector.

FIG. 11 is a cross-sectional view illustrating the internal configuration of the second connector.

DESCRIPTION OF EMBODIMENTS

First Embodiment

An example of a blood pressure measurement device 1 according to a first embodiment of the present invention will be described below with reference to FIGS. 1 to 11. FIG. 1 is an explanatory view illustrating a configuration of the blood pressure measurement device 1 according to the first embodiment, and FIG. 2 is a perspective view of the configuration of the blood pressure measurement device 1. FIG. 3 is a block diagram illustrating the configuration of the blood pressure measurement device 1. FIG. 4 is a perspective view illustrating a configuration of a height detection unit. FIG. 5 is a cross-sectional view illustrating a configuration of a first connector, FIG. 6 is a perspective view of the first connector, and FIG. 7 is a cross-sectional view of the first connector. FIG. 8 is a perspective view illustrating a configuration of a water head pressure bag. FIG. 9 is a perspective view illustrating a configuration of a second connector, and FIG. 10 is an explanatory view of the second connector, and is a partially cutout perspective view illustrating an internal structure. FIG. 11 is a cross-sectional view illustrating an internal configuration of the second connector. The blood pressure measurement device 1 is an electronic blood pressure measurement device attached to a living body 101. In the present embodiment, an electronic blood pressure measurement device attached to an upper arm of the living body 101 will be described.

As illustrated in FIG. 1, the blood pressure measurement device 1 includes a cuff 11 attached to a subject 100, a device body 20 mounted at a predetermined measurement location, and a connecting unit 50 connecting the cuff 11 and the device body 20.

The cuff 11 includes a bag-like cover body 14 wrapped around a living body 101, for example, here, an upper arm, and one or more air bags 15 (bag bodies) accommodated within the bag-like cover body 14.

The bag-like cover body 14 is formed from a sheet-like member such as cloth in a rectangular bag shape that is long in one direction. A hook-and-loop fastener or the like for fixing, for example, the cuff 11 to an upper arm is provided at a predetermined location in a front surface of the bag cover body 14. A hole portion 14a into which a tube unit 53 is inserted is formed in the bag-like cover body 14. The bag-like cover body 14 is wrapped around a living body such that the longitudinal direction of the bag-like cover body 14 extends along the circumferential direction of the living body. The air bag 15 is accommodated in the bag-like cover body 14.

Here, the air bag 15 is a bag-like structure, and since in the present embodiment, the blood pressure measurement device 1 uses air by a pump 22, the air bag 15 will be described. However, in a case where fluid other than air is used, the bag-like structure may be a fluid bag such as a liquid bag.

The air bag 15 is formed in a rectangular shape that is long in one direction. The air bag 15 is formed, for example, by combining two sheet members that are long in one direction, and thermally welding edges of the sheet members. The air bag 15 includes an opening that communicates with an internal space, and a connecting portion 15a having a tubular shape and extending along a surface direction of the cuff 11. A first air plug 54c of the connecting unit 50 described below is inserted into and connected to the connecting portion 15a.

The cuff 11 is fluidly connected to the pump 22 via the connecting unit 50 and is inflated by feeding of fluid by the pump 22. The cuff 11 is wrapped around the living body 101 such that the longitudinal direction of the cuff 11 extends along the circumferential direction of the living body 101, and is inflated to apply pressure to a blood vessel at a site of the subject 100 to which the cuff 11 is attached.

As illustrated in FIGS. 1 to 3, the device body 20 includes a housing 21, the pump 22 accommodated in the housing 21, an on-off valve 23, a pressure sensor 24, a power supply unit 27, a control substrate 28, an operation unit 29, and a display unit 31.

The housing 21 accommodates the pump 22, the on-off valve 23, the pressure sensor 24, a portion of the operation unit 29, a portion of the display unit 31, and the control substrate 28 and exposes the portion of the operation unit 12 and the portion of the display unit 31 from an outer surface of the housing 21. At a predetermined location in the outer surface of the housing 21, a connecting portion 21c including a plug hole 21a and a terminal connecting portion 21b is formed. The plug hole 21a is, for example, a hole portion that connects to a flow path portion, and can be fitted to a second air plug 56c of the connecting unit 50 described below. The terminal connecting portion 21b is provided adjacent to the plug hole 21a in the same surface as the surface in which the plug hole 21a is formed. The terminal connecting portion 21b includes the same number of hole portions as the number of terminals of communication terminals 57a of the connecting unit 50 described below.

The pump 22 is a pump device that feeds gas (air), and is, for example, a piezoelectric pump. The pump 22 compresses air and feeds compressed air to the cuff 11 via a flow path and the tube unit 53 formed in the device body 20. The pump 22 is electrically connected to a control unit 43.

A plurality of the on/off valves 23 are provided in a flow path formed in the device body 20, for example. Each of the on/off valves 23 opens and closes a portion of the flow path. A flow path leading from the pump 22 to the cuff 11 is selectively opened and closed by a combination of opening and closing each of the on/off valves 23.

The pressure sensor 24 is provided, for example, in the flow path leading from the pump 22 to the cuff 11, and detects pressure in the flow path communicating with the cuff 11. The pressure sensor 24 is electrically connected to the control substrate 28, converts detected pressure into an electrical signal, and outputs the electrical signal to the control substrate 28. The pressure sensor 24 measures internal pressure of the cuff 11 and blood pressure.

As illustrated in FIG. 3, the power supply unit 27 is, for example, a rechargeable battery such as a lithium ion battery. The power supply unit 27 is electrically connected to the control substrate 28 and supplies power to the control substrate 28.

The control substrate 28 includes, for example, a communication unit 41, a storage unit 42, and the control unit 43. The control substrate 28 is formed by mounting the communication unit 41, the storage unit 42, and the control unit 43 on a substrate.

The display unit 31 displays detected blood pressure information, contents of an operation, and the like.
The operation unit 29 includes an operation button, a touch panel, and the like for performing measurement settings and various kinds of input.

The communication unit 41 can transmit and receive information to and from an external device wirelessly or by wire. For example, the communication unit 41 transmits information such as information controlled by the control unit 43, a measured blood pressure value, and a pulse to an external device via a network and receives a program or the like for software update from an external device via a network and sends the program or the like to the control unit 43.

In the present embodiment, the network is, for example, the Internet, but is not limited to this. The network may be a network such as a Local Area Network (LAN) provided in a hospital or may be direct communication with an external device using a cable or the like including a terminal of a predetermined standard such as a USB. Thus, the communication unit 41 may include a plurality of elements such as a wireless antenna and a micro-USB connector.

The storage unit 42 pre-stores program data for controlling all the blood pressure measurement device 1 and a fluid circuit, settings data for setting various functions of the blood pressure measurement device 1, calculation data for calculating a blood pressure value and a pulse from pressure measured by the pressure sensor 24 or a water head pressure sensor 57, and the like. Additionally, the storage unit 42 stores information such as a measured blood pressure value and a measured pulse, and information such as water head pressure.

The control unit 43 includes one or more CPUs, and controls an operation of all the blood pressure measurement device 1 and an operation of the fluid circuit. The control unit 43 is electrically connected to and supplies power to the display unit 31, the operation unit 29, the pump 22, each of the on-off valves 23 and the pressure sensor 24, and the water head pressure sensor 57. Additionally, the control unit 43 controls operations of the display unit 31, the pump 22, and the on-off valve 23, based on electrical signals output by the operation unit 29, the pressure sensor 24, and the water head pressure sensor 57. For example, when a command to measure blood pressure is input, the control unit 43 drives the pump 22 and the on-off valve 23 to feed compressed air to the cuff 11. Additionally, the control unit 43 controls driving and stopping of the pump 22 and opening and closing of the on-off valve 23, based on an electrical signal output by the pressure sensor 24, selectively feeds compressed air to the cuff 11, and selectively pressurizes the cuff 11.

Additionally, the control unit 43 determines a measurement result such as fluctuation of a pulse wave, a blood pressure value such as maximum blood pressure and minimum blood pressure, a heart rate, and a posture of the subject 100 from electrical signals output by the pressure sensor 24 and the water head pressure sensor 57, and outputs an image signal corresponding to the measurement result to the display unit 31, or causes the storage unit 42 to store the measurement result.

In the device body 20 described above, the control unit 43 performs processing by using program data stored in the storage unit 42, and continuously generates blood pressure data from a pulse wave detected by the sensor. The blood pressure data includes data of a blood pressure waveform corresponding to a waveform of a measured pulse wave. The blood pressure data may further include time series data of a blood pressure feature value (blood pressure value). The blood pressure feature value includes, for example, systolic blood pressure (SBP) and diastolic blood pressure (DBP), but is not limited to this. A maximum value in a pulse wave waveform per heart rate corresponds to systolic blood pressure, and a minimum value in a pulse wave waveform per heart rate corresponds to diastolic blood pressure.

The connecting unit 50 includes the tube unit 53 including a cuff tube 51 that is a first tube and a water head pressure tube 52 that is a second tube, a first connector 54 provided in a first end side of the tube unit 53, a water head pressure bag 55 accommodated inside the first connector 54, a second connector 56 provided in a second end side of the tube unit 53, and the water head pressure sensor 57 accommodated in the second connector 56.

The cuff tube 51 has, for example, an inner diameter of φ6 mm, an outer diameter of φ10 mm, and constitutes a first flow path through which air that is first fluid passes. The cuff tube 51 is formed from a softer material than a material of the water head pressure tube 52. As an example, the cuff tube 51 is formed from, for example, a vinyl chloride-based resin material such as PVC (polyvinyl chloride), and formed in a tubular shape. The cuff tube 51 includes a first connecting tube portion 51a in a first end side and a second connecting tube portion 51b in a second end side. The first connecting tube portion 51a is inserted into and connected to the first connector 54, and the second connecting tube portion 51b is inserted into and connected to the second connector 56.

The water head pressure tube 52 is disposed in the cuff tube 51. The water head pressure tube 52 has a smaller flow path diameter than a flow path diameter of the cuff tube 51, and is narrow and has an inner diameter of φ2 mm and an outer diameter of φ3 mm, for example. The water head pressure tube 52 constitutes a second flow path through which second fluid 70 passes. Additionally, the water head pressure tube 52 is formed from a material that is harder and more rigid than the material of the cuff tube 51, for example, a fluorine-based resin such as PTFE (polytetrafluoroethylene), and formed in a tubular shape. The water head pressure tube 52 has higher bending rigidity than bending rigidity of the cuff tube 51.

The tube unit 53 is a double tube in which the water head pressure tube 52 that is the second tube is disposed in the first flow path in the cuff tube 51 that is the first tube. The tube unit 53 has a length of approximately 1500 mm.

In the present embodiment, a height detection unit 35 that detects positional relationship in the height between the cuff 11 and the device body 20 includes the water head pressure bag 55 provided in the air bag 15 side, the water head pressure sensor 57 provided in the device body 20, and the water head pressure tube 52 connected to the water head pressure bag 55 and the water head pressure sensor 57.

As illustrated in FIGS. 4 to 8, the first connector 54 integrally includes a first case body 54a including the first air plug 54c connected to the cuff 11, and a second case body 54b that accommodates the water head pressure bag 55. The first connector 54 includes the first case body 54a and the second case body 54b that are continuously aligned along the axial direction of the tube unit 53 and that are fluid-tightly defined. The first connector 54 is formed from a thin connector having a smaller dimension in the thickness direction than a dimension in the width direction.

The first case body 54a is formed in a rectangular parallelepiped shape and formed from, for example, a synthetic resin, and forms the flow path of the first fluid. A first tube hole 54d to which the cuff tube 51 of the tube unit 53 is connected is formed in a first side wall of the first case body 54a. A second tube hole 54e that is coaxial with the first tube hole 54d is formed in a second side wall of the first case body 54a. The first tube hole 54d is formed in a circular shape having a diameter equal to an outer diameter of the first connecting tube portion 51a of the cuff tube 51. The second tube hole 54e is formed in a circular shape having a diameter equal to an outer diameter of a joint portion 55c of the water head pressure bag 55. Additionally, the first air plug 54c that protrudes outward is formed in the second side wall of the first case body 54a. The first air plug 54c is formed in a cylindrical shape and communicates a flow path in the first case body 54a with a flow path portion of the device body 20. The first air plug 54c extends along the main surface direction of the first connector 54.

The second case body 54b is formed in a rectangular parallelepiped shape and forms a sealed accommodation space accommodating the water head pressure bag 55. The second case body 54b is fixed to the second side wall of the first case body 54a. A third tube hole 54f is a through hole facing and communicating with the second tube hole 54e, and is formed in a first side wall of the second case body 54b. The third tube hole 54f is coaxial with the second tube hole 54e and is formed in the same shape as the shape of the second tube hole 54e. The water head pressure tube 52 passes through the first tube hole 54d, the second tube hole 54e, and the third tube hole 54f that are coaxially disposed, and passes through the first case body 54a into the second case body 54b. Additionally, the first air plug 54c extends in parallel to the direction in which the plurality of tube holes are aligned, that is, the direction in which the water head pressure tube 52 extends.

The first connector 54 is disposed in the bag-like cover body 14 of the cuff 11, and inside the bag-like cover body 14, the first air plug 54c is inserted into the connecting portion 15a of the air bag 15 and fluidly connects the first connector 54 to the air bag 15.

As illustrated in FIG. 8, the water head pressure bag 55 is connected to a first end side of the water head pressure tube 52. The water head pressure bag 55 is, for example, a flat fluid bag, and an inside of the water head pressure bag 55 is filled with the second fluid 70. The water head pressure bag 55 includes a bag portion 55a having a flat and circular shape. The bag portion 55a integrally includes a protrusion portion 55b including an outer peripheral edge partly protruding in the radial direction, and the joint portion 55c having a circular tubular shape and being continuous with the protrusion portion 55b.

The bag portion 55a is accommodated in the second case body 54b. The bag portion 55a is deformable according to an increase and a decrease in an amount of the second fluid accommodated inside the bag portion 55a.

For example, from the bag portion 55a through the protrusion portion 55b and the joint portion 55c to the water head pressure tube 52, the water head pressure bag 55 includes no recess and protrusion in an inner surface of the water head pressure bag 55 and is subjected to less fluid resistance. Thus, for example, in filling with the second fluid 70, the water head pressure tube 52 side is disposed in an upper side and air is easily released toward the water head pressure tube 52 side.

The second fluid 70 is, for example, fluid having a smaller compression rate than a compression rate of the first fluid, and in the present embodiment, for example, glycerin having specific gravity of 1.26 g/cm$^3$ is used.

The second connector 56 integrally includes a third case body 56a including the second air plug 56c and a fourth case body 56b that accommodates the water head pressure sensor 57. The fourth case body 56b and the third case body 56a are continuously aligned along the axial direction of the tube unit 53 and fluid-tightly defined. The second connector 56 is formed from a thin connector having a smaller dimension in the thickness direction than a dimension in the width direction.

The third case body 56a is formed from a synthetic resin and has a flat shape including, for example, an outer peripheral wall having an arc shape. The third case body 56a forms a portion of the flow path of the first fluid. A fourth tube hole 56d is formed in a first side wall of the third case body 56a. In a second side wall of the third case body 56a, a fifth tube hole 56e penetrating the side wall is formed coaxially with the fourth tube hole 56d. The second air plug 56c protruding in the thickness direction of the second connector 56 is formed in a bottom wall portion constituting a first main surface of the third case body 56a. The second air plug 56c is formed in a cylindrical shape and forms the flow path through which the first fluid passes.

The fourth case body 56b is formed in a rectangular parallelepiped shape and accommodates the water head pressure sensor 57. A sixth tube hole 56f is a through hole facing and communicating with the fifth tube hole 56e, and is formed in a first side wall of the fourth case body 56b. The water head pressure sensor 57 is accommodated inside the fourth case body 56b. A plurality of hole portions 56g through which the communication terminals 57a of the water head pressure sensor 57 pass are formed in a bottom wall portion constituting a first main surface of the fourth case body 56b. The communication terminals 57a extend from the fourth case body 56b and protrude in the protruding direction of the second air plug 56c.

The fourth tube hole 56d is a circular hole portion having an inner diameter equal to an outer diameter of the second connection tube portion 51b, and the second connecting tube portion 51b in the second end side of the cuff tube 51 is inserted into and connected to the fourth tube hole 56d. Additionally, the fifth tube hole 56e and the sixth tube hole 56f each have an inner diameter equal to the outer diameter of the water head pressure tube 52, and the water head pressure tube 52 passes through the fourth tube hole 56d and the fifth tube hole 56e into the fourth case body 56b.

The second connector 56 is connected to the connecting portion 21c of the device body 20. Specifically, the second air plug 56c of the second connector 56 is inserted into the plug hole 21a of the housing 21, and the communication terminals 57a are inserted into the terminal connecting portion 21b of the housing 21. The second air plug 56c is inserted into the plug hole 21a and the communication terminals 57a are inserted into the terminal connecting portion 21b, and thus the second connector 56 is electrically and mechanically connected to the device body 20, and the flow path portion of the device body 20 communicates with the tube unit 53.

For example, in the present embodiment, the device body 20 and a cuff unit 10 including the connecting unit 50 connected to and integrally assembled with the cuff 11 are separate components. For example, a user inserts the second connector 56 into the device body 20 and connects the cuff unit 10 and the device body 20.

The water head pressure sensor 57 is a pressure sensor accommodated in the fourth case 56b. The water head pressure sensor 57 is connected to a second end side of the water head pressure tube 52 and detects pressure of the second fluid 70 in the flow path communicating with the water head pressure bag 55. The water head pressure sensor 57 includes the plurality of communication terminals 57a protruding outside the fourth case 56b. The water head pressure sensor 57 is electrically connected to the control substrate 28, converts detected pressure into an electrical signal, and outputs the electrical signal to the control substrate 28.

Pressure of the second fluid detected by the water head pressure sensor 57 is proportional to a difference in the height between the water head pressure sensor 57 and the water head pressure bag 55. The water head pressure sensor 57 is provided in the device body 20 side, that is, near the pressure sensor 24 that measures blood pressure. On the other hand, the water head pressure bag 55 is attached to the cuff 11 side. That is, the positional relationship in the height between the cuff 11 and the device body 20 can be detected by the water head pressure sensor 57.

The blood pressure measurement device 1 according to an embodiment configured in this manner includes the configuration where the water head pressure tube 52 through which the second fluid 70 for water head pressure detection passes is disposed in the first flow path of the cuff tube 51 through which the first fluid for blood pressure measurement passes. Thus, the number of lines of tubing can be reduced by combining the tubing for blood pressure measurement and the tubing for water head pressure measurement into single double tubing, and usability improves.

In the blood pressure measurement device 1, the water head pressure tube 52 in which the second fluid 70 having a small compression rate is disposed is disposed through the inside of the cuff tube 51 of the first fluid having a large compression rate, and thus deformation of the water head pressure tube 52 can be prevented and water head pressure detection accuracy can be maintained. Moreover, the tube unit 53 itself can be bent, and thus handleability can be ensured. Additionally, damage to the water head pressure tube 52 can be prevented by covering an outer periphery of the water head pressure tube 52 with the cuff tube 51 of air, and fluid leakage can be prevented. Additionally, according to the blood pressure measurement device 1, the first connector 54 including the first case body 54a and the second case body 54b, and the second connector 56 including the third case body 56a and the fourth case body 56b are provided, and thus connection of the water head pressure tube 52 can be performed easily. Additionally, the flow paths of the two kinds of fluids can be separated and fluid leakage can be prevented with a simple configuration by the first connector 54 and the second connector 56.

Additionally, according to the blood pressure measurement device 1, in the second connector 56, the second air plug 56c and the communication terminals 57a protrude in the same direction, and thus electrical connection and connection of the flow path can be performed by single connection work, and workability and handleability improve. Additionally, an inner wall in the tube connecting side of the water head pressure bag 55 includes a smooth front surface without recess or protrusion. Thus, when the second fluid 70 is sealed during manufacture, air can be released toward the water head pressure tube 52 side of the water head pressure bag 55 simply by placing the water head pressure tube 52 side in the upper side. Thus, air can be prevented from entering the water head pressure bag 55, and detection accuracy of water head pressure can be maintained.

Further, the second fluid is glycerin having low volatility, and thus generation of air in the water head pressure bag can be suppressed, and measurement accuracy can be ensured.

However, the embodiments described above are merely examples of the present invention in all respects. Needless to say, various modifications and variations can be made without departing from the scope of the present invention. That is, a specific configuration in accordance with an embodiment may be adopted as appropriate in carrying out the present invention.

REFERENCE SIGNS LIST

1 Blood pressure measurement device
10 Cuff unit
11 Cuff
14 Bag-like cover body
15 Air bag
20 Device body
21 Housing
21a Plug hole
21b Terminal connecting portion
21c Connecting portion
22 Pump
23 On-off valve
24 Pressure sensor
27 Power supply unit
28 Control substrate
29 Operation unit
31 Display unit
41 Communication unit
42 Storage unit
43 Control unit
50 Connecting unit
51 Cuff tube
52 Water head pressure tube
53 Tube unit
54 First connector
54a First case body
54b Second case body
54c First air plug
54d First tube hole
54e Second tube hole
54f Third tube hole
55 Water head pressure bag
55a Bag portion
55b Protrusion portion
55c Joint portion
56 Second connector
56a Third case body
56b Fourth case body
56c Second air plug
56d Fourth tube hole
56e Fifth tube hole
56f Sixth tube hole
56g Hole portion
57 Water head pressure sensor
57a Communication terminal
100 Subject
101 Living body

The invention claimed is:

1. A blood pressure measurement device comprising:
a cuff comprising a bag body including an internal space in which first fluid is disposed, the cuff being configured to be wrapped around a living body;
a device body comprising a pressure sensor configured to detect pressure of the first fluid in a flow path portion communicating with the internal space of the bag body;
a first tube constituting a first flow path through which the first fluid passes, the first tube including a first end side connected to the bag body and a second end side connected to the device body;
a second tube disposed in the first flow path in the first tube and constituting a second flow path through which second fluid passes;
a water head pressure bag provided in a first end side of the second tube and accommodating the second fluid, the water head pressure bag being attached to the cuff; and
a water head pressure sensor provided in a second end side of the second tube and configured to detect pressure of the second fluid.

2. The blood pressure measurement device according to claim 1, further comprising the first fluid and the second fluid, wherein
the water head pressure sensor is attached to the device body,
the second fluid has a smaller compression rate than a compression rate of the first fluid, and
the second tube has a smaller flow path diameter and higher bending rigidity than a flow path diameter and bending rigidity of the first tube.

3. The blood pressure measurement device according to claim 2, wherein the device body comprises the flow path portion connected to the internal space of the bag body via the first tube, a pump configured to feed the first fluid to the bag body via the flow path portion, an on-off valve configured to open and close the flow path portion, a control unit configured to control operations of the pump and the on-off valve, and a housing, including an outer surface, provided with a connecting portion to which a tube unit, including the first tube and the second tube, is connected.

4. The blood pressure measurement device according to claim 3, integrally comprising a first case body and a second case body, the first case body being connected to the first end side of the first tube and including a space in which the first tube communicates with the internal space of the bag body, the second case body accommodating the water head pressure bag connected to the first end side of the second tube, and the blood pressure measurement device comprising a first connector attached to the cuff.

5. The blood pressure measurement device according to claim 2, integrally comprising a first case body and a second case body, the first case body being connected to the first end side of the first tube and including a space in which the first tube communicates with the internal space of the bag body, the second case body accommodating the water head pressure bag connected to the first end side of the second tube, and the blood pressure measurement device comprising a first connector attached to the cuff.

6. The blood pressure measurement device according to claim 2, integrally comprising a third case body and a fourth case body, the third case body connected to the first tube and forming a flow path in which the flow path portion in the device body communicates with the first tube, the fourth case body accommodating the water head pressure sensor connected to the second tube, and the blood pressure measurement device comprising a second connector connected to the device body.

7. The blood pressure measurement device according to claim 2, wherein the second fluid is glycerin.

8. The blood pressure measurement device according to claim 1, wherein the device body comprises the flow path portion connected to the internal space of the bag body via the first tube, a pump configured to feed the first fluid to the bag body via the flow path portion, an on-off valve configured to open and close the flow path portion, a control unit configured to control operations of the pump and the on-off valve, and a housing, including an outer surface, provided with a connecting portion to which a tube unit, including the first tube and the second tube, is connected.

9. The blood pressure measurement device according to claim 8, integrally comprising a first case body and a second case body, the first case body being connected to the first end side of the first tube and including a space in which the first tube communicates with the internal space of the bag body, the second case body accommodating the water head pressure bag connected to the first end side of the second tube, and the blood pressure measurement device comprising a first connector attached to the cuff.

10. The blood pressure measurement device according to claim 8, integrally comprising a third case body and a fourth case body, the third case body connected to the first tube and forming a flow path in which the flow path portion in the device body communicates with the first tube, the fourth case body accommodating the water head pressure sensor connected to the second tube, and the blood pressure measurement device comprising a second connector connected to the device body.

11. The blood pressure measurement device according to claim 8, further comprising the first fluid and the second fluid, wherein
the second fluid has a smaller compression rate than a compression rate of the first fluid, and
the second fluid is glycerin.

12. The blood pressure measurement device according to claim 1, integrally comprising a first case body and a second case body, the first case body being connected to the first end side of the first tube and including a space in which the first tube communicates with the internal space of the bag body, the second case body accommodating the water head pressure bag connected to the first end side of the second tube, the blood pressure measurement device comprising a first connector attached to the cuff.

13. The blood pressure measurement device according to claim 12, integrally comprising a third case body and a fourth case body, the third case body connected to the first tube and forming a flow path in which the flow path portion in the device body communicates with the first tube, the fourth case body accommodating the water head pressure sensor connected to the second tube, and the blood pressure measurement device comprising a second connector connected to the device body.

14. The blood pressure measurement device according to claim 12, further comprising the first fluid and the second fluid, wherein
the second fluid has a smaller compression rate than a compression rate of the first fluid, and
the second fluid is glycerin.

15. The blood pressure measurement device according to claim 1, integrally comprising a third case body and a fourth case body, the third case body connected to the first tube and forming a flow path in which the flow path portion in the device body communicates with the first tube, the fourth case body accommodating the water head pressure sensor connected to the second tube, the blood pressure measurement device comprising a second connector connected to the device body.

16. The blood pressure measurement device according to claim 15, wherein
the third case body comprises a plug having a tubular shape and protruding outward, and
the water head pressure sensor comprises a terminal protruding from the fourth case body in a protruding direction of the plug.

17. The blood pressure measurement device according to claim 16, further comprising the first fluid and the second fluid, wherein
the second fluid has a smaller compression rate than a compression rate of the first fluid, and
the second fluid is glycerin.

18. The blood pressure measurement device according to claim 15, further comprising the first fluid and the second fluid, wherein
the second fluid has a smaller compression rate than a compression rate of the first fluid, and
the second fluid is glycerin.

19. The blood pressure measurement device according to claim 1, further comprising the first fluid and the second fluid, wherein
the second fluid has a smaller compression rate than a compression rate of the first fluid, and
the second fluid is glycerin.

20. A cuff unit comprising:
a cuff connected to a device body and comprising a bag body including an internal space in which first fluid is disposed, the cuff being configured to be wrapped around a living body;
a first tube constituting a first flow path through which the first fluid passes, the first tube including a first end side connected to the bag body and a second end side connected to the device body;
a second tube disposed in the first flow path in the first tube and constituting a second flow path through which second fluid passes;

a water head pressure bag provided in a first end side of the second tube and accommodating the second fluid, the water head pressure bag being attached to the cuff; and a water head pressure sensor provided in a second end side of the second tube and configured to detect pressure of the second fluid.

\* \* \* \* \*